(12) United States Patent
Chou et al.

(10) Patent No.: US 9,770,462 B2
(45) Date of Patent: Sep. 26, 2017

(54) METHOD OF TREATING OVARIAN, TUBAL AND PERITONEAL CANCER

(71) Applicants: NATIONAL CHENG KUNG UNIVERSITY, Tainan (TW); NATIONAL CHENG KUNG UNIVERSITY HOSPITAL, Tainan (TW)

(72) Inventors: Cheng-Yang Chou, Tainan (TW); Tien-En Kuo, Houston, TX (US); Yu-Fang Huang, Kaohsiung (TW)

(73) Assignees: National Cheng Kung University, Tainan (TW); National Cheng Kung University Hospital, Tainan (TW)

( * ) Notice: Subject to any disclaimer, the term of this patent is extended or adjusted under 35 U.S.C. 154(b) by 0 days.

(21) Appl. No.: 14/874,937

(22) Filed: Oct. 5, 2015

(65) Prior Publication Data
US 2017/0095492 A1    Apr. 6, 2017

(51) Int. Cl.
| | |
|---|---|
| *A61K 31/132* | (2006.01) |
| *A61K 31/704* | (2006.01) |
| *A61K 31/555* | (2006.01) |
| *A61K 45/06* | (2006.01) |

(52) U.S. Cl.
CPC .......... *A61K 31/704* (2013.01); *A61K 31/132* (2013.01); *A61K 31/555* (2013.01); *A61K 45/06* (2013.01)

(58) Field of Classification Search
CPC .................................................. A61K 31/132
See application file for complete search history.

(56) References Cited

U.S. PATENT DOCUMENTS

| | | |
|---|---|---|
| 2006/0013819 A1 | 1/2006 | Kelsey |
| 2011/0287110 A1* | 11/2011 | Dewhirst ............... A61K 31/27 424/649 |

OTHER PUBLICATIONS

Fu et al (Mol Cancer Ther Jun. 2012 11; 1221).*
BC Cancer Agency Cancer Drug Manual (2006, Doxorubin, pegylated liposomal, pp. 1-10).*
NIH Dictionary (https://www.cancer.gov/publications/dictionaries/cancer-drug?cdrid=39424, accessed Nov. 11, 2016).*

* cited by examiner

*Primary Examiner* — Benjamin Packard
(74) *Attorney, Agent, or Firm* — Rosenberg, Klein & Lee

(57) ABSTRACT

A method of treating ovarian, tubal and peritoneal cancer is revealed. It comprises administering an effective amount of a pharmaceutical composition (including a copper chelator, a platinum-based chemotherapeutic agent and an anthracycline) to a subject in need thereof for reducing concentration of intracellular copper ions and promoting activation of transcription factor Sp1 and human copper transporter 1 (hCTR1).

7 Claims, 8 Drawing Sheets

METHOD OF TREATING OVARIAN, TUBAL AND PERITONEAL CANCER

BACKGROUND OF THE INVENTION

1. Field of the Invention

The present invention relates to a method of treating ovarian, tubal and peritoneal cancer, especially for applying a pharmaceutical composition comprising a copper chelator, a platinum-based chemotherapeutic agent and an anthracycline to a subject in need thereof. The copper chelator lowers intracellular copper ion levels and promoting activation of transcription factor Sp1 and human copper transporter 1 (hCTR1), resulting in an increased uptake of the platinum-based chemotherapeutic agent as well as the anthracycline, and reduced proliferation of cancer cells.

2. Description of Related Art

Growing evidence implicates tubal cancer, ovarian cancer, and so-called primary peritoneal carcinomas as having a common origin, pathogenesis, and behavior (*Annu Rev Pathol.* 2014; 9:27-45). Hence, ovarian cancer cell lines are usually used for in-vitro and animal studies for these three cancers. Regarding the treatment, the NCCN Guidelines discuss fallopian tube cancer and primary peritoneal cancer that are managed in a similar manner to epithelial ovarian cancer. In the clinic, these cancers are treated with the same chemotherapeutic agents even when they recur after primary therapy. Additionally, clinical trials for ovarian cancer are commonly designed to enroll patients with these three cancers.

Usually, tubal cancer, ovarian cancer, and primary peritoneal carcinomas are found at a late stage. According to NCCN Clinical Practice Guidelines in Oncology, these patients are generally administered with platinum-based chemotherapeutic compounds after a debulking operation. However, cancer cells treated with platinum-based chemotherapeutic drugs frequently develop chemoresistance and result in treatment failure. Hence, an increased dosage of drugs or different strategies for improving the treatment against chemoresistant cancer cells is necessary.

Currently a variety of treatment strategies are developed, e.g. liposomal doxorubicin, hycamtin and the like. However, the use of these second-line drugs may not enhance the treatment efficacy. As a result, the mortality rate remains high due to cancer recurrence. Additionally, US Patent Pub. No. 2006/0013819, have disclosed a method for treating platinum-resistant, ovarian cancer, primary peritoneal carcinoma or fallopian tube carcinoma with the combination of a HER2 antibody that effectively inhibits HER dimerization as well as gemcitabine. However, the therapeutic effect of abovementioned method is still limited.

The present inventors found that copper chelator can lower intracellular copper ion levels and increase Sp1 and hCTR1 activation, allowing chemotherapeutic agents to be transported into ovarian cancer cells in basic research. Furthermore, they also observed significantly treatment effect in animal experiments.

Nowadays there are numerous chemotherapeutic agents on the market. Therefore, how to develop a pharmaceutical composition comprising copper chelating agents in combination with chemotherapeutic agents for overcoming chemoresistance of these three cancers is still an important goal in cancer therapy.

SUMMARY OF THE INVENTION

In view of the above-mentioned problems, the object of the present invention is to provide a pharmaceutical composition which can be used to treat ovarian, tubal and peritoneal cancer by reducing concentration of intracellular copper ions and promoting activation of transcription factor Sp1 and human copper transporter 1 (hCTR1), so as to increase uptake of the platinum-based chemotherapeutic agent and the anthracycline by chemoresistant cancer cells.

Disclosed herein is a method of treating ovarian, tubal and peritoneal cancer by administering an effective amount of a pharmaceutical composition to a subject in need thereof for reducing concentration of intracellular copper ions and promoting activation of transcription factor Sp1 and human copper transporter 1 (hCTR1), wherein the pharmaceutical composition comprises a copper chelator, a platinum-based chemotherapeutic agent and an anthracycline.

According to an embodiment of the present invention, the copper chelator is tetrathiomolybdate, trientine or D-penicillamine.

According to an embodiment of the present invention, the platinum-based chemotherapeutic agent is cisplatin or carboplatin; the anthracycline is pegylated liposomal doxorubicin, doxorubicin or epirubicin.

According to an embodiment of the present invention, the copper chelator is trientine, the platinum-based chemotherapeutic agent is carboplatin, and the anthracycline is pegylated liposomal doxorubicin.

According to an embodiment of the present invention, the subject in need of such treatment is first administered with the copper chelator, and subsequently with the platinum-based chemotherapeutic agent and the anthracycline.

According to an embodiment of the present invention, the pharmaceutical composition is administered orally or parenterally, preferably the pharmaceutical composition is administered orally.

Accordingly, the pharmaceutical composition containing the copper chelator is able to promote entry of the platinum-based chemotherapeutic agent into chemoresistant cancer cells for effectively treating ovarian, tubal and peritoneal cancer.

DETAILED DESCRIPTION OF THE PREFERRED EMBODIMENT

Figure 1:
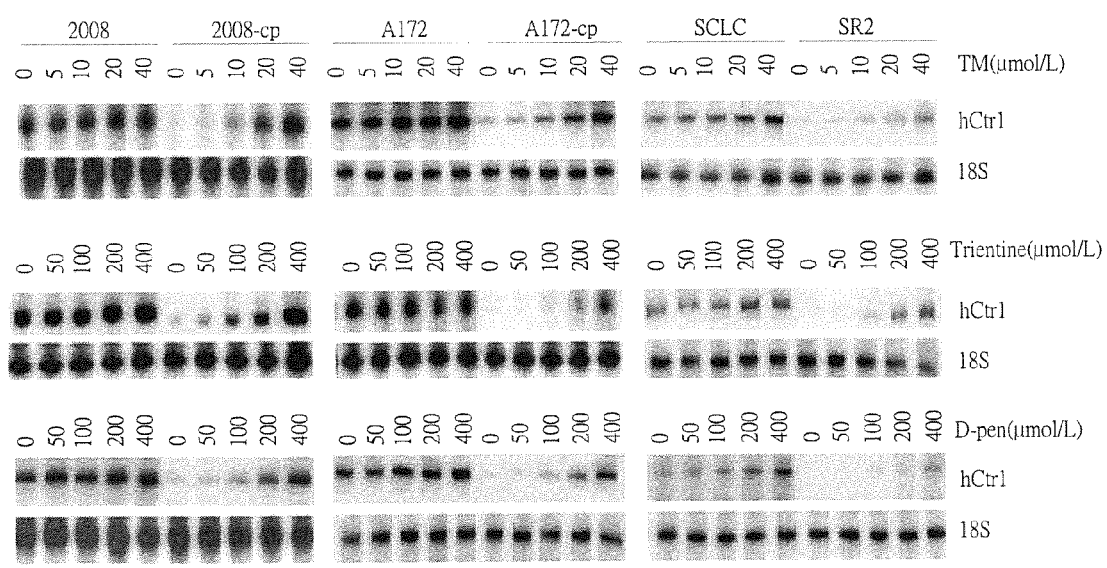
FIG. 1 is a diagram showing that copper chelators enhances hCTR1 mRNA levels in cisplatin-resistant (cDDP$^R$) and cisplatin-sensitive (cDDP$^S$) cells.

A method of treating ovarian, tubal and peritoneal cancer is disclosed, which administers an effective amount of a pharmaceutical composition to a subject in need of such treatment for reducing concentration of intracellular copper ions and promoting activation of transcription factor Sp1 and human copper transporter 1 (hCTR1), wherein the pharmaceutical composition comprises a copper chelator, a platinum-based chemotherapeutic agent and an anthracycline. According to the above description, the copper chelator is tetrathiomolybdate, trientine or D-penicillamine; the platinum-based chemotherapeutic agent is cisplatin or carboplatin; and the anthracycline is pegylated liposomal doxorubicin, doxorubicin, or epirubicin.

Preferably, the copper chelator is trientine, the platinum-based chemotherapeutic agent is carboplatin, and the anthracycline is pegylated liposomal doxorubicin. The subject in need is first administered with the copper chelator, and subsequently with the platinum-based chemotherapeutic agent and the anthracycline.

The pharmaceutical composition is administered orally or parenterally. Herein, the term "parenteral delivery" includes subcutaneous, intradermic, intravenous, intramuscular, intra-articular, intra-arterial, synovial, intrapleural, intrathecal, local, and intracranial injections. In addition, the term "treating" used in the present invention refers to the application or administration of the pharmaceutical compositions to a subject with symptoms or tendencies of suffering from ovarian, tubal and peritoneal cancer in order to cure, heal, alleviate, relieve, alter, remedy, ameliorate, improve, prevent or affect the symptoms or tendencies of these three cancers. Furthermore, "an effective amount" used herein refers to the amount of the pharmaceutical carrier required to confer therapeutic effect on the subject. The effective amount may vary according to the route of administration, excipient usage, and co-usage with other active ingredients.

Hereinafter, an exemplary embodiment of the present invention will be described in detail with reference to the accompanying drawings.

Example 1: hCTR1 Expression in Chemoresistant and Chemosensitive Cell Lines

The cell lines used in this study were obtained from the following sources: ovarian cancer cell lines 2008 and 2008-cp from Dr. Z. Siddik (MD Anderson Cancer Center, Houston, Tex.), human glioblastoma cell lines A172 and A172-Cp from Dr. A. Gomi (Jichi Univ., Tokyo, Japan), small cell lung cancer cell lines SCLC and SR2 from N. Savaraj, (Univ. Miami). Three pairs of cisplatin (Cp) resistant cell lines (cDDP$^R$) (2008-cp, A172-cp and SR2) and their matched parental cells (2008, A172 and SCLC) were treated with different concentrations of three different copper chelators (Cu depletors), tetrathiomolybdate (TM) (0, 5, 10, 20 and 40 μmol/L), trientine (0, 50, 100, 200 and 400 μmol/L) or D-penicillamide (D-pen) (0, 50, 100, 200 and 400 μmol/L). Cisplatin (Cp), carboplatin, oxaliplatin, tetrathiomolybdate (TM), trientine, and D-penicillamide (D-pen) were obtained from Sigma-Aldrich (St Luis, Mo.). The hCTR1 expression levels were estimated by RNase Protection Assay. 18S RNA was used as an internal control.

As shown in FIG. 1, all three Cu depletors enhanced the hCtr1 expression in all three cDDP$^R$ cell lines and their drug-sensitive counterparts. In addition, the magnitudes of enhancement of hCtr1 mRNA expression in the cDDP$^R$ cells were greater (ranging from 15- to 20-fold) than in the respective drug-sensitive lines (<50% increase) as analyzed by densitometry analysis.

Furthermore, $^{64}$Cu uptake and platinum (Pt) uptake, and sensitization to cisplatin and carboplatin in three pairs of cDDP$^R$ cell lines (2008-cp, A172-cp and SR2) and cDDP$^S$ cell lines (2008, A172 and SCLC) in the absence or presence of copper chelator (5 μmol/L of TM, 100 μmol/L of trientine or 100 μmol/L of D-pen) were evaluated.

Figure 2:
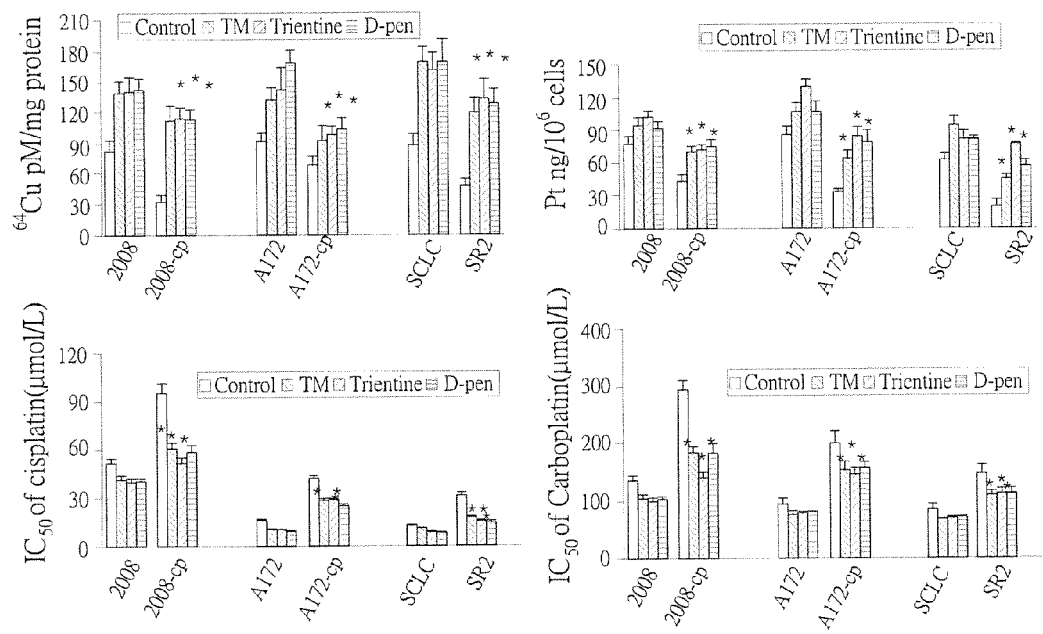
FIG. 2 is a diagram showing that the higher increases in hCtr1 expression levels in the treated cisplatin-resistant (cDDP$^R$) cells corresponds with higher increases in $^{64}$Cu and platinum (Pt) uptake.

As shown in FIG. 2, the higher increases in hCtr1 expression levels in the treated cDDP$^R$ cells lines (2008-cp, A172-cp and SR2) correspond with higher increases in $^{64}$Cu and Pt uptake, and in sensitivity of cells to cisplatin. Enhanced hCtr1 expression was also correlated with an increased sensitivity to carboplatin, albeit to a lesser extent than that to Pt, but not to oxaliplatin (data not shown). These results demonstrate that Cu depletors can reverse Pt resistance in cDDP$^R$ cells by enhancing hCtr1 expression.

Example 2: Copper Chelator and Platinum-Based Chemotherapeutic Agent Act Synergistically to Inhibit Tumor Growth Female athymic NCR nu/nu-nude mice (aged 5 weeks, weight ~20 grams) were purchased from the National Cancer Institute-Frederick Cancer Research and Development Center (Frederick, Md.) and housed in a pathogen-free environment. Animal care followed the guidelines of the Association for Assessment and Accreditation of Laboratory Animal Care. The animal protocol was approved by the MDACC Institutional Animal Care and Use Committee.

The animals were inoculated subcutaneously with $5 \times 10^6$ cancer cells on the dorsal lumbosacral region. About one month later, when the tumor volumes reached 150-250 mm$^3$, the animals were randomly divided into four groups with four animals per group and the treatments were initiated: the first group (control) was treated with 100 μl of 0.85% NaCl solution by gavage. The second group (D-pen) was treated with 100 μl of 400 mM D-pen (in 0.85% NaCl) by daily gavage for 28 days. The third group (Cp) was intravenously injected with Cp (5 mg/kg) four times at intervals of 7 days. The fourth group (Cp+D-pen) was treated with Cp and D-pen following the combined treatment schedules as described in the second and third groups respectively.

Tumor growth was evaluated weekly by measuring the tumor volume according to the following formula: tumor volume=width$^2$×length×0.5. The tumor growth rate (%) was calculated as tumor volume at the final time point/initial tumor volume×100%. One week after the last treatment, two randomly selected mice from each group were euthanized and necropsied. The hCTR1 and Sp1 expression levels were estimated by RNase Protection Assay. 18S RNA was used as an internal control.

Figure 3:
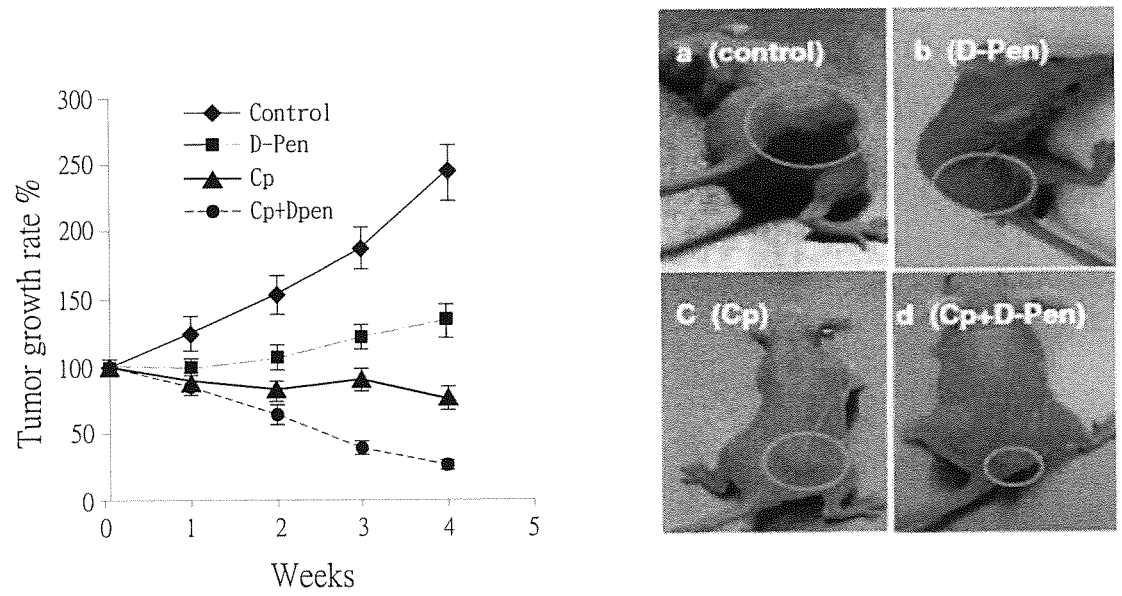
FIG. 3 is a diagram showing that copper chelator (D-Pen) and platinum-based chemotherapeutic agent (Cp) act synergistically to inhibit tumor growth.

As shown in FIG. 3, tumor sizes in the representative animals from each group at the end of the treatment are circled. Animals treated with D-pen and Cp (Cp+D-pen) show decreased tumor size than that of treated with D-pen or Cp alone. These results demonstrate that D-pen and Cp act synergistically to inhibit tumor growth.

Figure 4:
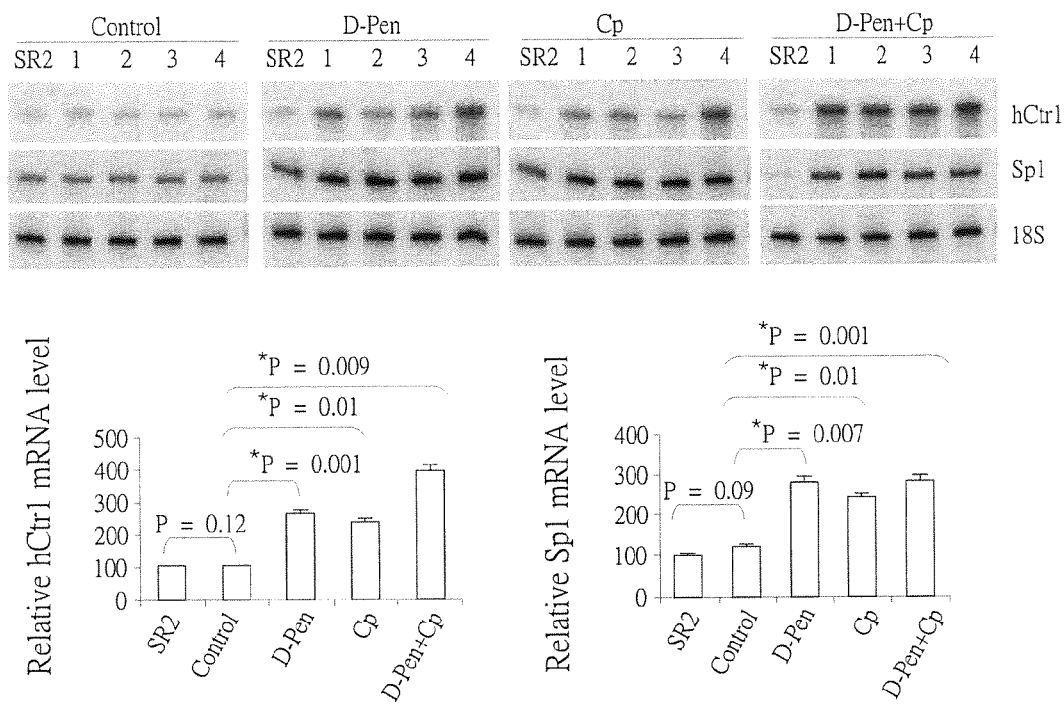
FIG. 4 is a diagram showing animals have increased hCtr1 and Sp1 mRNA expression in the residual tumors after treated with copper chelator (D-Pen) and platinum-based chemotherapeutic agent (Cp)

As shown in FIG. 4, h Ctrl and Sp1 mRNA expression in the residual tumors in each animal as determined. Animals treated with D-pen and Cp (Cp+D-pen) show enhanced hCtr1 and Sp1 mRNA expression than that of treated with D-pen or Cp alone.

Example 3: FOXM1 Downregulates the Expression of hCTR1 and SP1

It is well known that FOXM1 is required for cell cycle progression, apoptosis, angiogenesis, and DNA damage repair. In addition, FOXM1 plays a critical role of the maintenance of stem cell pluripotency. For instance, aberrant expression of FOXM1 is linked to tumorigenesis and chemoresistance. Accordingly, effects of FOXM1 on hCTR1 and SP1 in Ad293 cells expressing vector alone (pcDNA), vector encoding FOXM1, control siRNA (siControl), or FOXM1 siRNA (siFOXM1) were measured herein by Western blots. β-ACTIN was used as an internal control.

Cell lysates were harvested in ice-cold modified radioimmune precipitation assay buffer containing a protease inhibitor Cocktail™ (Roche). Lysates normalized for amount protein were separated on 10% SDS-polyacrylamide gels and electrophoretically transferred to nitrocellulose (Hybond™-P PVDF transfer membranes; Amersham Biosciences). After incubation with primary antibodies to FOXM1, SP1 or hCTR1 (Santa Cruz), the membrane was incubated with HRP-conjugated secondary antibody to detect immunocomplexes. Antibody binding was detected by enhanced chemiluminescence (ECL detection kit, Amersham) followed by exposure to X-ray films or the BioSpectrum® Imaging System (UVP).

Figure 5:
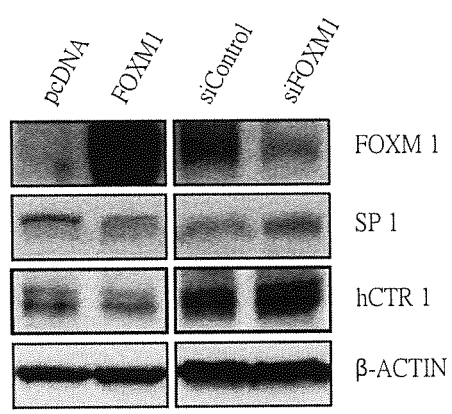
FIG. 5 is a diagram showing that knockdown of FOXM1 (siFOXM1) enhances the expression of hCTR1 and SP1.

As shown in FIG. 5, FOXM1 affects the expression of hCTR1, which transports cisplatin into cells to elicit a cytotoxic effect. Overexpression of FOXM1 in the cells decreased amounts of hCTR1 and its regulatory transcription factor SP1, whereas knockdown of FOXM1 (siFOXM1) via RNA interference increased amounts of hCTR1 and SP1. These findings suggest that FOXM1 promotes cisplatin resistance by impairing cisplatin uptake.

Example 4: Knockdown of IMP3 or Lin28B Increases Expression of hCTR1 and the Cisplatin Sensitivity RNA-binding proteins, IMP3 and Lin28B, are known to induce cell proliferation, migration, and invasion. Herein, effects of IMP3 or Lin28B Knockdown on hCTR1 expression and cisplatin sensitivity were measured. Western blot was used to determine hCTR1 expression in in different ovarian cancer cell lines, including shControl cells (shControl), Lin28B knockdown cells (shLin28B-860, shLin28B-508) and IMP3 knockdown cells (shIMP3-268, shIMP3-596). β-actin was used as an internal control.

Cell lysates were harvested in ice-cold modified radioimmune precipitation assay buffer containing a protease inhibitor Cocktail™ (Roche). Lysates normalized for amount protein were separated on 10% SDS-polyacrylamide gels and electrophoretically transferred to nitrocellulose (Hybond™-P PVDF transfer membranes; Amersham Biosciences). After incubation with primary antibodies to hCTR1 (Santa Cruz), the membrane was incubated with HRP-conjugated secondary antibody to detect immunocomplexes. Antibody binding was detected by enhanced chemiluminescence (ECL detection kit, Amersham) followed by exposure to X-ray films or the BioSpectrum® Imaging System (UVP).

The cytotoxicity of shControl cells (shControl), IMP3 knockdown cells (shIMP3-268, shIMP3-596) and Lin28B knockdown cells (shLin28B-860, shLin28B-508) in response to cisplatin was determined using the WST-1 (TaKaRa) assay. In brief, $3 \times 10^4$ ovarian cancer cells/well were grown in 96-well plates overnight and treated with cisplatin at various concentrations in the presence or absence of copper ions (3000 µM) (Copper Histidine) for 24 hours. After incubation, the CellTiter-Glo Cell Viability Assay (Promega) was used to determine the $IC_{50}$ of cisplatin. Dose-inhibition curves and the $IC_{50}$ of cisplatin were calculated for the different cell types using commercial software (SigmaPlot V10.0, Systat Software, Inc., Richmond, Calif., USA). A copper histidine solution was prepared. In brief, copper(II) chloride (0.106 g; Sigma-Aldrich) and L-histidine (0.244 g; Sigma-Aldrich) were dissolved in 90 ml of sterile 0.9% sodium chloride, titrated to a pH of 738 to 7.40, and then filtered through a 0.22-µm filter before use.

Figure 6:
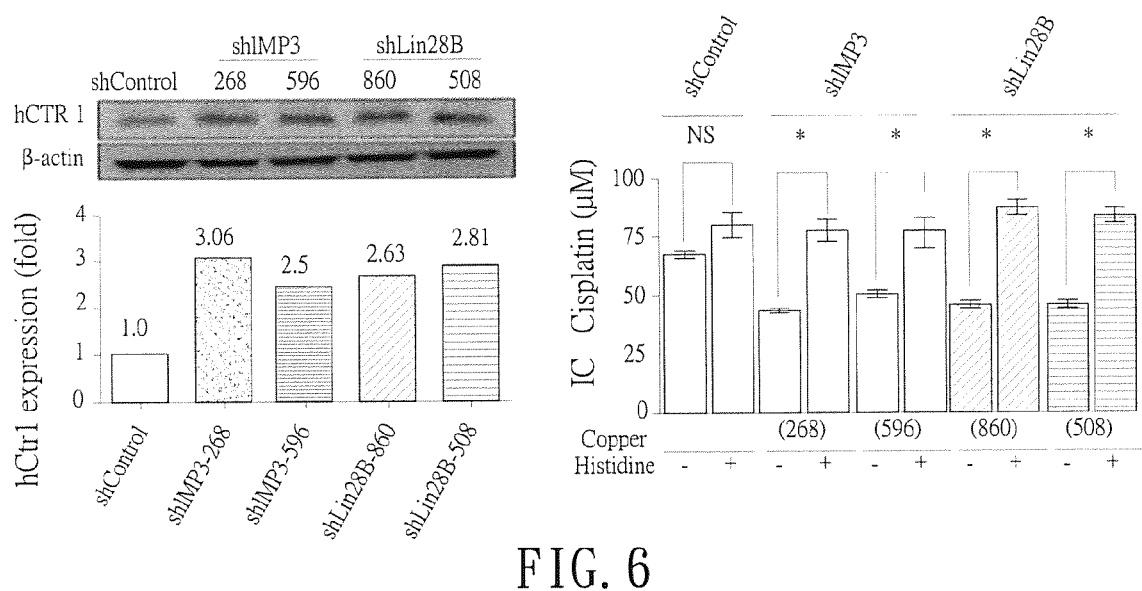
FIG. 6 is a diagram showing that knockdown of IMP3 (shIMP3) or Lin28B (shLin28B) enhances the expression of hCTR1.

As shown in FIG. 6, both of IMP3-knockdown cells (shIMP3) and Lin28B-knockdown cells (shLin28B) showed increased expression of hCTR1. In addition, the $IC_{50}$ values increased in IMP3- or Lin28B-knockdown cells when combined with copper histidine (*p<0.05) while no significant (NS) effect was observed in shControl cells.

To analyze hCTR1 expression correlated with IMP3 and Lin28B expression in advanced ovarian, tubal, primary peritoneal carcinomas, immunohistochemistry was performed. Formalin fixed tissues from patients were processed in 4 µm thick sections on glass slides. After blocking endogenous peroxidase activity, the sections were subjected to heat-induced antigen retrieval using an autoclave. After incubation with the hCTR1 primary antibody (1:500, Novus Biologicals), binding was detected using a biotin-labelled secondary antibody and the ABC complex method (LSAB kit; DAKO).

As shown in Table 1, most tumors with high hCTR1 expression also expressed low levels of IMP3 and Lin28B. In contrast, tumors with low hCTR1 expression expressed high levels of IMP3 and Lin28B (p=0.009 and 0.003, respectively). Furthermore, patients with high hCTR1 expression had a longer progression-free survival (PFS) than those with low hCTR1 expression (p 0.0035, log-rank test).

TABLE 1

|  |  | hCTR1 | | |
| --- | --- | --- | --- | --- |
|  | RNA expression | High (n = 40) | Low (n = 40) | p |
| IMP3 | High | 16(40.0%) | 27(67.5%) | 0.009 |
|  | Low | 24(60.0%) | 13(32.5%) |  |
| Lin28B | High | 14(35.0%) | 27(67.5%) | 0.003 |
|  | Low | 26(35.0%) | 13(32.5%) |  |

Example 5: Copper Chelator, Platinum-Based Chemotherapeutic Agent and Anthracycline Act Synergistically to Inhibit Tumor Growth in Clinical Trial According to the above results which show inhibiting effects on cancers in cell lines models and animal models, the present inventors enrolled patients with these three cancers. Subjects were first administered with the copper chelator (trientine), and subsequently with the platinum-based chemotherapeutic agent (carboplatin) and the anthracycline (pegylated liposomal doxorubicin). In brief, subjects were orally and daily administered with trientine from day 1 to the last day of the treatment, and intravenously injected with carboplatin AUC 4 and pegylated liposomal doxorubicin (40 mg/m²) on day 8 every four weeks as a treatment cycle, continued for six treatment cycles.

Figure 7:
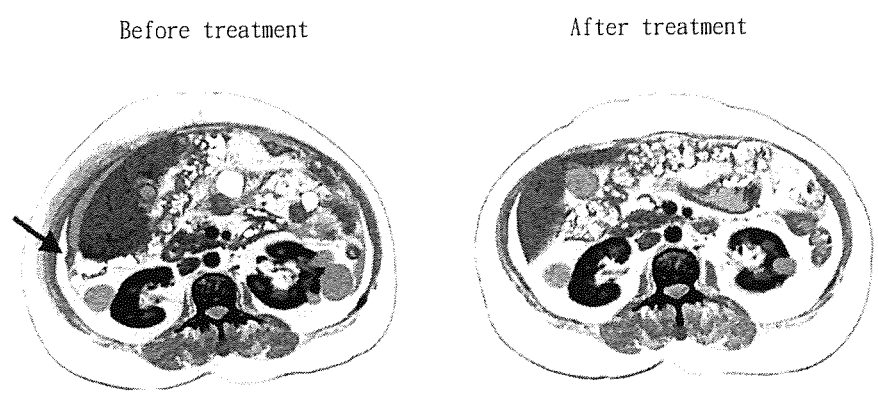
FIG. 7 is a diagram showing that copper chelator, platinum-based chemotherapeutic agent and anthracycline act synergistically to inhibit the spread of tumor nodules in human peritoneum.
Figure 8:
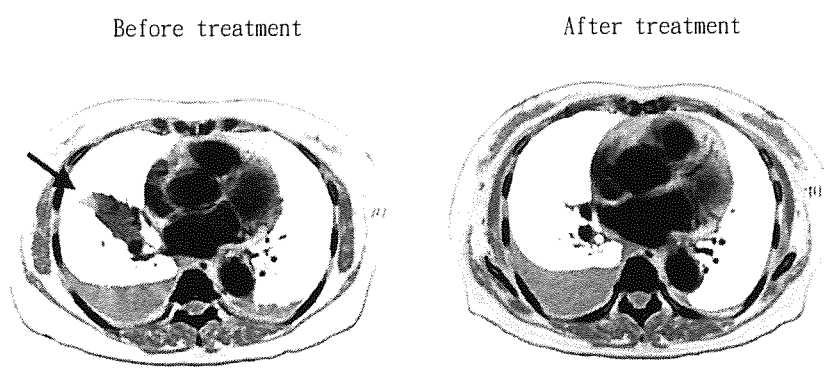
FIG. 8 is a diagram showing that copper chelator, platinum-based chemotherapeutic agent and anthracycline act synergistically to inhibit metastasis of tumor in human lung.

Results are illustrated in FIG. 7 and FIG. 8, treatment response is evaluated by computed tomography scan (CT scan), which shows tumor involvement of the peritoneum (FIG. 7) and the lung (FIG. 8) in two patients before and after the therapeutic combination of trientine, carboplatin and pegylated liposomal doxorubicin.

As shown in FIG. 7, the peritoneal lining was thickened with the presence of tumor nodules (as indicated by the arrow) before treatment whereas the peritoneal nodule and ascitic fluid were absent after treatment.

As shown in FIG. 8, an irregular metastatic nodule in the right lung with the presence of pleural effusion (as indicated by the arrow) before treatment whereas the right lung nodule was absent after treatment.

According to the above description, the present therapy and pharmaceutical composition related to copper chelator for ovarian, tubal and primary peritoneal cancer can overcome platinum resistance and increase chemotherapy response.

What is claimed is:

1. A method of treating ovarian, tubal and peritoneal cancer, comprising:

administering an effective amount of a pharmaceutical composition to a subject in need of such treatment during a four-week treatment cycle for reducing concentration of intracellular copper ions and promoting activation of transcription factor Sp1 and human copper transporter 1 (hCTR1), wherein the pharmaceutical composition comprises a copper chelator, a platinum-based chemotherapeutic agent and pegylated liposomal doxorubicin;

administering the copper chelator from an initial treatment day to day 28 of the four-week treatment cycle; and, administering the platinum-based chemotherapeutic agent and the pegylated liposomal doxorubicin at day 8 of the four-week treatment cycle.

2. As the method claimed in claim 1, wherein the copper chelator is tetrathiomolybdate, trientine or D-penicillamine.

3. As the method claimed in claim 1, wherein the platinum-based chemotherapeutic agent is cisplatin or carboplatin.

4. As the method claimed in claim 1, wherein the copper chelator is trientine, and the platinum-based chemotherapeutic agent is carboplatin.

5. As the method claimed in claim 1, wherein the subject in need is first administered with the copper chelator, and subsequently with the platinum-based chemotherapeutic agent and the pegylated liposomal doxoribicin.

6. As the method claimed in claim 1, wherein the pharmaceutical composition is administered orally or parenterally.

7. As the method claimed in claim 6, wherein the copper chelator is administered orally and the platinum-based chemotherapeutic agent and the pegylated liposomal doxorubicin are administered parenterally.

* * * * *